United States Patent [19]

Pritchard

[11] Patent Number: 4,924,854
[45] Date of Patent: May 15, 1990

[54] DETECTION DEVICES

[75] Inventor: Alan Pritchard, Bangor, Northern Ireland

[73] Assignee: Mectet Industries Limited, Belfast, Northern Ireland

[21] Appl. No.: 303,186

[22] Filed: Jan. 30, 1989

[30] Foreign Application Priority Data

Jan. 29, 1988 [GB] United Kingdom ............... 8801968

[51] Int. Cl.⁵ ................................................ A61B 1/06
[52] U.S. Cl. .................................................... 128/6
[58] Field of Search ..................................... 128/6, 7

[56] References Cited

U.S. PATENT DOCUMENTS 4,294,234 10/1981 Matsuo ................................. 128/6

Primary Examiner—William H. Grieb
Attorney, Agent, or Firm—Sixbey, Friedman, Leedom & Ferguson

[57] ABSTRACT

A detection device comprising a longitudinally extending hollow body (7) having a light input position (11) located transversely between the ends thereof, one end comprising an output or viewing window end (10) and the other end comprising an output/input window end (b 12). Light transmissive fibres are provided to connect between the light input position (11) and the output/input window end (12) and between such output/input window end (12) and the viewing window end (10). Means (17, 18) are provided to facilitate varying the angle of incidence of light rays impinging on the fibres (21) located at the light input position (11) so as to facilitate focusing the length of focus of light rays emitted from the fibres (22) at the output portion at the output/input window end (12) to be reflected back to the fibres (23) of the input portion at the output/input window end (12).

10 Claims, 3 Drawing Sheets

DETECTION DEVICES

The invention relates to detection devices and to such devices utilising fibre optics, more particularly but not exclusively, to such devices for use in clinical or medical diagnosis.

There are presently available many fibre optic devices, normally known as endoscopes, which enable a person to view, as an extension of the eye, positions which are not accessible directly to the eye, for example within the human body and in many instances in industry. Such devices are extremely expensive and do not have the capacity to "see into" the object being investigated.

It is an object of the invention to provide a device which can be produced at a fraction of the cost of presently known devices and which can "see into" the object being investigated.

According to one aspect of the invention there is provided a detection device comprising a longitudinally extending hollow body having a light input position located transversely between the ends thereof, one end comprising an output or viewing window end and the other end comprising an output/input window end, light transmissive fibres being provided to connect between the light input position and the output/input window end and between such output/input window end and the viewing window end, means being provided to facilitate varying the angle of incidence of light rays impinging on the fibers located at the light input position so as to facilitate focussing the length of focus of light rays emitted from the fibres at the output portion at the output/input window to be reflected back to the fibres of the input portion at the output/input window.

According to a further aspect of the invention there is provided a detection device comprising a longitudinally extending hollow body having at one end a light output-/input detection window a bundle of light transmissive fibres being located adjacent such window, a portion of such bundle being diverted to a light input position with their ends located transversely of the ends of the body and the remainder of such bundle being with their ends located adjacent the other end of the body which comprises a viewing window.

The arrangement of the next preceding paragraph can be used with great advantage in combination with the arrangement of the next but one preceding paragraph.

The means for facilitating the angle of incidence of light rays inpinging on the fibres located at the light input position may comprise relatively rotatable members where the body is cylindrical and an aperture is formed therein to provide the light input. Ideally the apertured cylindrical body is rotatable relative to the light input. A rotatable member may be attached to the body for causing adjustment of such aperture and/or for locking relative such members in position.

An air gap may be provided which is located between the light input position and the fibres located at the light input position. Furthermore a light impermeable barrier may be located between the input fibres and the output fibres adjacent the light input position.

The outer portions of the fibres at the input position may be arranged at an angle to the outer portions of the input fibres and be rotatable relative thereto in order to control the angle of incidence of light rays being omitted from fibres at the input position to the fibres at the light input position within the body.

Bundles of light transmissive fibres may be removably attachable at the output/input window position so as to provide a flexible extension of the output/input detection of the object being investigated. Furthermore there may be provided a bundle of light transmissive fibres from a light source to the light input position of the hollow body. With such an arrangement the body may be separable and may be such that it can be sterilised by autoclave if required.

The foregoing and further features of the invention may be more readily understood from the following description of preferred embodiments by way of example, with reference to the accompanying drawings in which.

Figure 1:
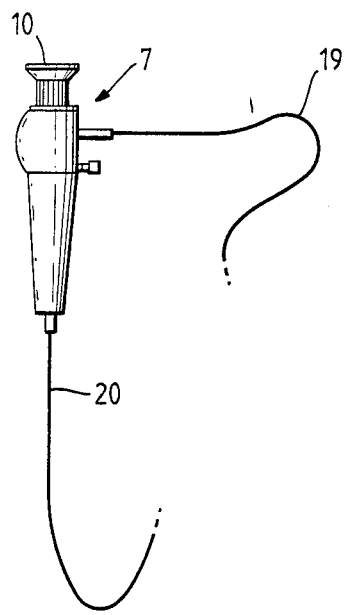
FIG. 1 is a diagrammatic illustration of an embodiment of the invention.

Referring now to the drawings there is shown a device which is particularly for detecting the presence of Meconium or coloured fluids in the amniotic fluid surrounding a feotus prior to birth.

Figure 2:
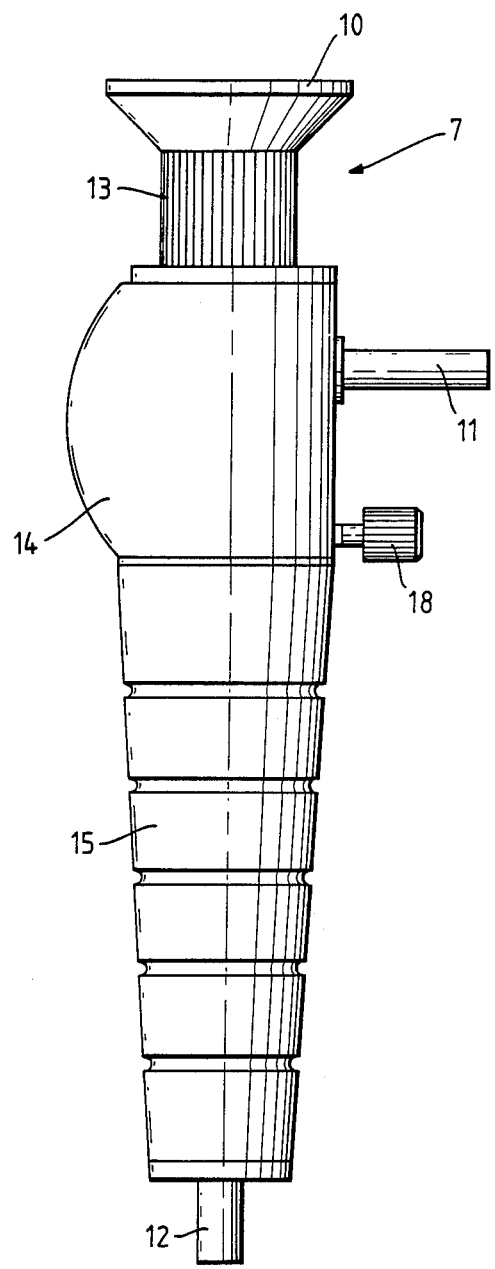
FIG. 2 is a side elevational view on an enlarged scale of the body member of the embodiment of FIG. 1.
Figure 3:
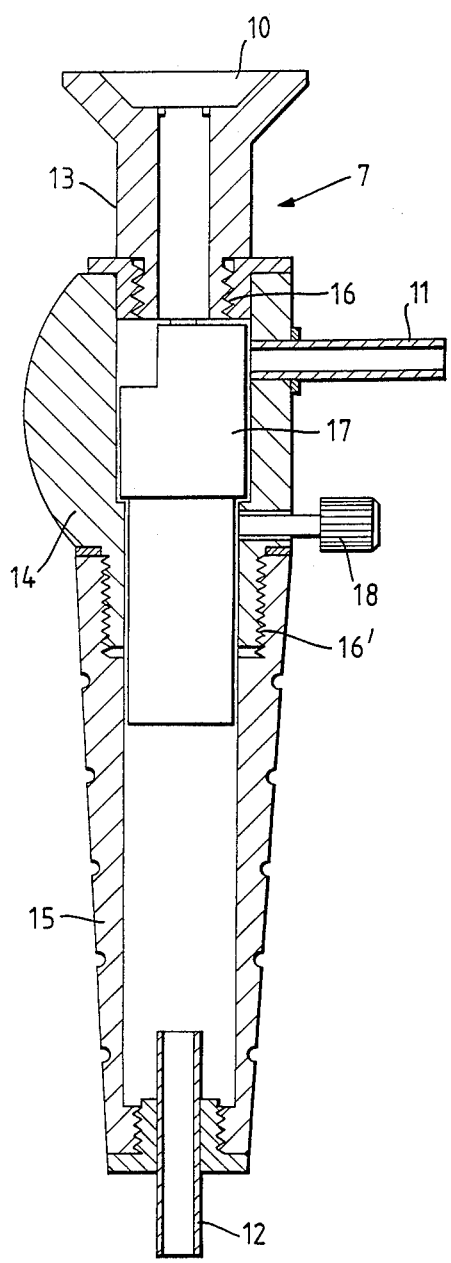
FIG. 3 is a sectional view of the body member of FIG. 2.
Figure 5:
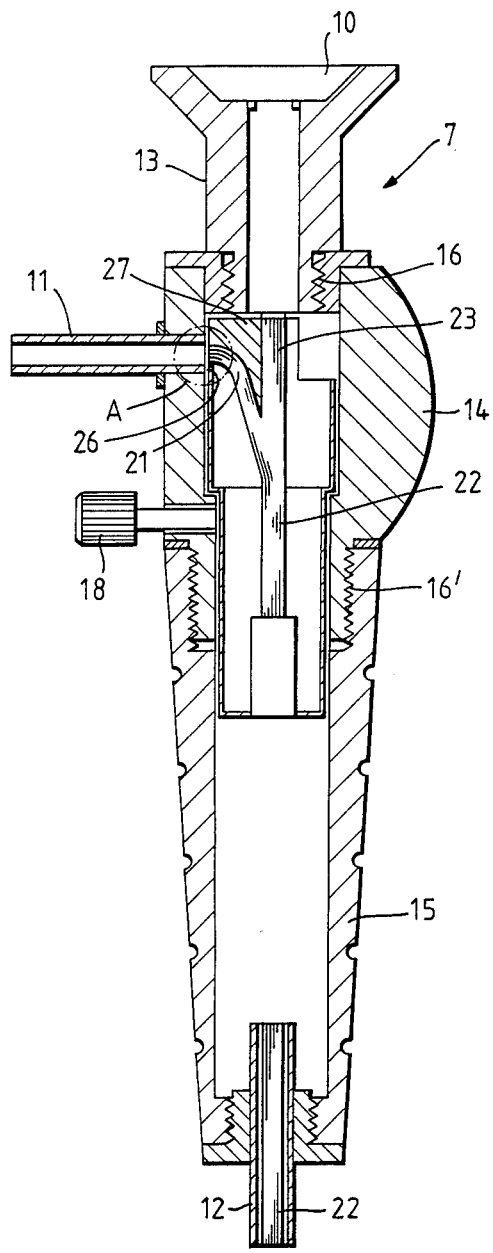
FIG. 5 is a similar view to that of FIG. 3 but showing more detail.

FIGS. 2, 3 and 5 show a hand held viewing device 7 at which there is a viewing aperture 10. A light input is applied at position 11 and is directed to an output/input position 12 via light transmissive fibres 22 (FIG. 5).

Further light transmissive fibres 23 are provided between the output/input position 12 to the viewing position 10. The viewing device 7 comprises an upper member 13 attached to body members 14 and 15. These are separable at screw threads 16 and 16' so that the members 14, 15 can be sterilised when used in a medical environment.

The outer portion of the device 7 is rotatable around a vertical axis relative to an inner portion 17 so that an aperture or window in portion 17 can provide a variable angle of incidence with light rays occurring at the light input applied at position 11 for focusing.

A screw threaded member 18 is provided which may be utilised for providing relative rotation between the body of device 7 and the aperture or window of portion 17.

In use a light input is provided at position 11 by light transmissive fibres 19 (FIG. 1). Such light input is directed to the output/input position 12 at which further light transmissive fibres 20 (FIG. 1) transmit such light to the distal end thereof.

Such distal end may be inserted within the cervix of a pregnant woman to be adjacent the membrane containing the aminiotic fluid and feotus and the focusing of such light emission, to the position within the membrane, is controlled as previously described at device 7. Many problems can occur with a feotus, such as bleeding or bowel movement due to the distress producing Meconuim in the amniotic fluid which causes discolouration of such fluid. Hence with the light output from the distal end being focused into the amniotic fluid between the membrane and the head of the feotus, the reflected light will show the colour of such fluid to indicate any problems or distress of the feotus to enable emergency action to be taken.

The light transmissive fibres may be of glass or synthetic plastics material. Within the body of device 7 the light transmissive fibres are preferably of extremely small diameter. A bundle of such fibres may be located at output/input end 12 and a portion located with their ends within input position 11 and the remainder with their ends adjacent viewing aperture 10 which may have a magnifying lens located therein.

Figure 4A:
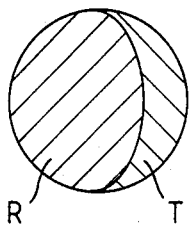
FIGS. 4a-4e show a cross-section of various fibre bundles that can be utilised with the device of FIGS. 2 and 3.
Figure 4B:
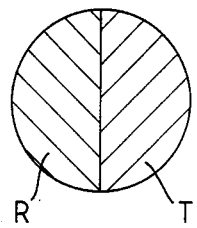
Figure 4C:
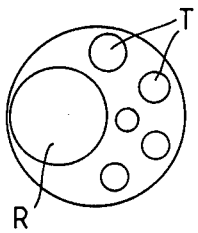
Figure 4D:
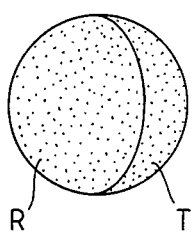
Figure 4E:
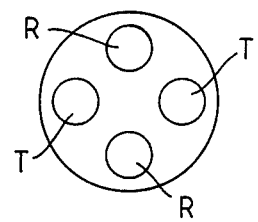

The "wandering lead" of light transmissive fibres to be attached to outout/input position 12 may be of the cross-sectional form as shown in FIGS. 4a to 4e. In each of these figures the portion t represents the area of fibres that transmit light whilst the portion R represents the area of fibres which receives light to be passed to viewing aperture 10. With the arrangements shown in FIGS. 4c and 4e it is necessary to accurately locate fibres 20 with respect to output/input position 12 but no such location is necessary with the arrangements shown in FIGS. 4a, 4b, and 4d. These latter are preferably by control of device 7 but the arrangements of FIGS. 4c and 4e are cheaper to produce.

Figure 6:
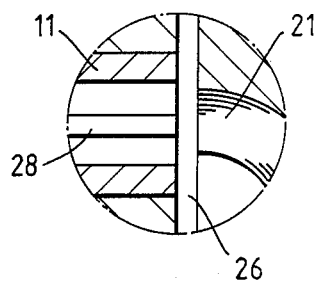
FIG. 6 shows the portion A of FIG. 5 on enlarged scale.

Referring now more particularly to FIGS. 5 and 6 a light impermeable member 27 is located between input fibres 21 and output fibres 22 so that there is no light emission therebetween.

With regard to FIG. 6 there is shown an air gap 26 between the input fibres at input position 11 and the input fibres 21 located within device 7. This air gap is provided to ensure that the angle of the output light rays from the fibres at input position 11 arrive at the outward end of fibres 21 such that the angle of incidence thereto is ensured.

Figure 7:
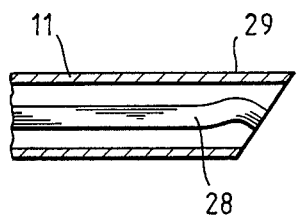
FIG. 7 is a diagrammatic view of a portion of an alternative embodiment.

With regard to FIG. 7 there is shown an alternative embodiment wherein the input position 11 has a facility of providing input fibres 28 having output ends at an angle to the vertical axis. In this embodiment the body 29 at input position 11 may be rotatable about the horizontal axis. With such an arrangement an angle of incidence of the light rays impinging upon fibres 21 are at such an angle that the depth of focus is enhanced at the distal end of the device 7.

Although the embodiment shown and described is for use in a medical/clinical situation, such device could be used in an industrial environment e.g. dyeing materials where colour is involved and needs to be detected.

I claim:

1. A detection device comprising a longitudinally extending hollow body having a light input position located transversely between the ends thereof, one end comprising an output or viewing window end and the other end comprising as output/input window end, light transmissive fibres being provided to connect between the light input position and the output/input window end and between such output/input window end and the viewing window end, means being provided to facilitate varying the angle of incidence of light rays impinging on the fibres located at the light input position so as to facilitate focusing the length of focus of light rays emitted from the fibres at the output portion at the output/input window end to be reflected back to the fibres of the output portion at the output/input window end.

2. A detection device as claimed in claim 1 wherein the means for facilitating the angle of incidence of light rays impinging on the fibres located at the light input position comprises relatively rotatable members where the body is cylindrical and an aperture is formed therein to provide the light input.

3. A detection device as claimed in claim 2 wherein the apertured cylindrical body is rotatable relative to the light input.

4. A detection device as claimed in claim 3 wherein a rotatable member is attached to the body for causing adjustment of such apertures.

5. A detection device as claimed in claim 3 wherein a rotatable member is attached to the body for locking such members in a predetermined position.

6. A detection deice as claimed in claim 1 wherein an air gap is located between the light input position and fibres located at the light input position.

7. A detection device as claimed in claim 1 wherein a light impermeable barrier is located between input fibres and output fibres adjacent light input position.

8. A detection device as claimed in claim 1 wherein the outer portions of the fibres at the input position are arranged at an angle to the outer portions of the input fibres and are rotatable relative thereto in order to further control the angle of incidence of light rays being emitted from fibres at the input position to the fibres at the light input position within the body.

9. A detection device as claimed in claim 1 wherein bundles of light transmissive fibres are removably attachable at the output/input window end so as to provide a flexible extension of the output/input end of the object being investigated.

10. A detection device as claimed in claim 1 wherein a bundle of light transmissive fibres are attached from a light source to the light input position of the hollow body.

* * * * *